United States Patent
Fierlbeck et al.

(10) Patent No.: US 9,675,393 B2
(45) Date of Patent: Jun. 13, 2017

(54) SHORTENING PALM SCREW

(71) Applicant: DePuy SYNTHES PRODUCTS, INC., West Chester, PA (US)

(72) Inventors: Johann Fierlbeck, Salzburg (AT); Alfred Niederberger, Salzburg (AT)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 894 days.

(21) Appl. No.: 13/622,159

(22) Filed: Sep. 18, 2012

(65) Prior Publication Data
US 2013/0253593 A1    Sep. 26, 2013

Related U.S. Application Data

(60) Provisional application No. 61/537,874, filed on Sep. 22, 2011, provisional application No. 61/539,185, filed on Sep. 26, 2011.

(51) Int. Cl.
| *A61B 17/80* | (2006.01) |
| *A61B 17/84* | (2006.01) |
| *A61B 17/68* | (2006.01) |
| *A61B 17/72* | (2006.01) |
| *A61B 17/74* | (2006.01) |
| *A61B 17/00* | (2006.01) |
| *A61B 17/17* | (2006.01) |

(52) U.S. Cl.
CPC ............ *A61B 17/844* (2013.01); *A61B 17/68* (2013.01); *A61B 17/8061* (2013.01); *A61B 17/1778* (2016.11); *A61B 17/7266* (2013.01); *A61B 17/746* (2013.01); *A61B 2017/00991* (2013.01)

(58) Field of Classification Search
CPC .... A61B 17/80; A61B 17/844; A61B 17/8061
USPC .............................. 606/286, 62, 63
See application file for complete search history.

(56) References Cited

U.S. PATENT DOCUMENTS

| 5,603,715 A | 2/1997 | Kessler |
| 2004/0097930 A1 | 5/2004 | Justis et al. |
| 2004/0153074 A1* | 8/2004 | Bojarski et al. ............... 606/72 |
| 2004/0193162 A1 | 9/2004 | Bramlet et al. |
| 2011/0066190 A1 | 3/2011 | Schaller et al. |

FOREIGN PATENT DOCUMENTS

| EP | 0 922 437 | 6/1999 |
| WO | 01/28443 | 4/2001 |

* cited by examiner

Primary Examiner — David Isabella
Assistant Examiner — Christine Nelson
(74) Attorney, Agent, or Firm — Fay Kaplun & Marcin, LLP

(57) ABSTRACT

An implant for treating a bone includes an outer sleeve extending longitudinally from a proximal end to a distal end and including a lumen extending therethrough and an inner element sized and shaped to be slidably received within the lumen of the outer sleeve, the inner element extending longitudinally from a proximal end received within the lumen to a distal end including a bone-engaging element, the implant movable between an expanded configuration in which the inner element is in a distal-most position relative to the outer sleeve and a shortened configuration in which the inner element slides proximally relative to the outer element.

9 Claims, 13 Drawing Sheets

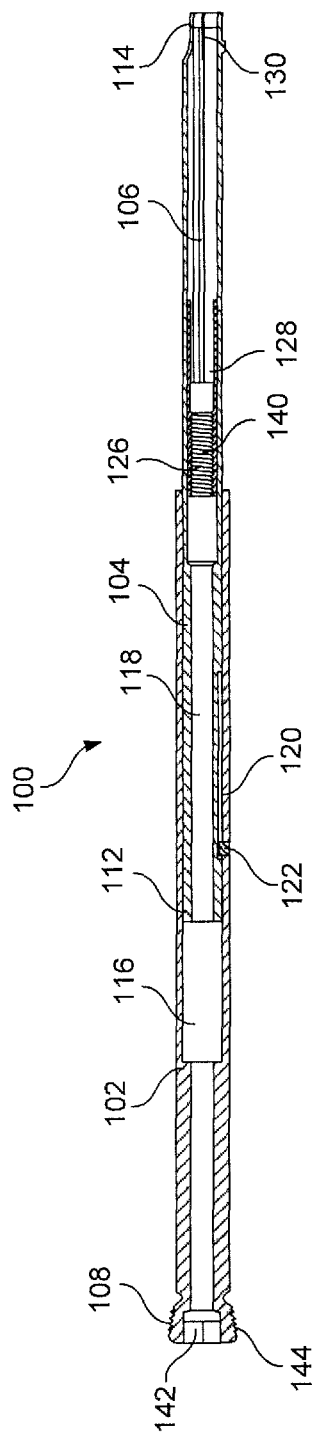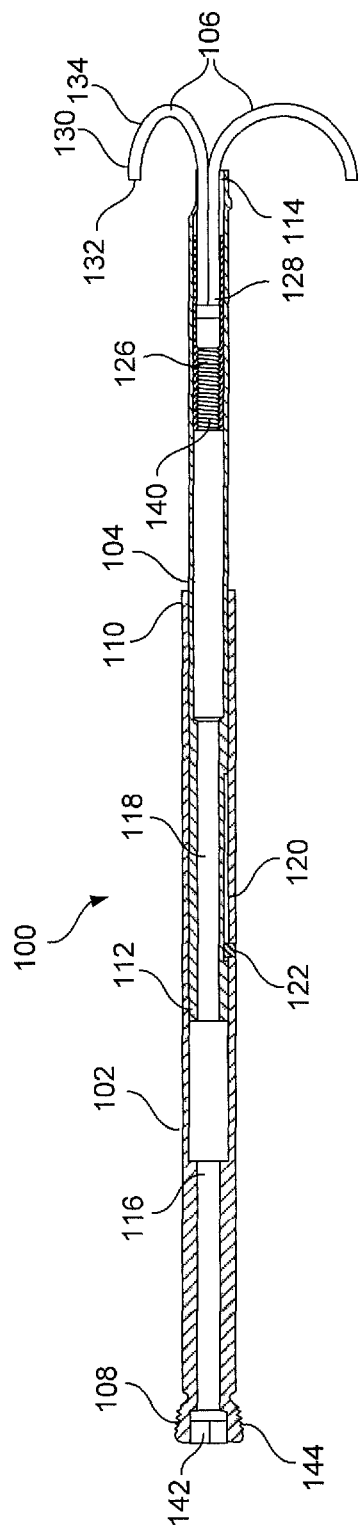

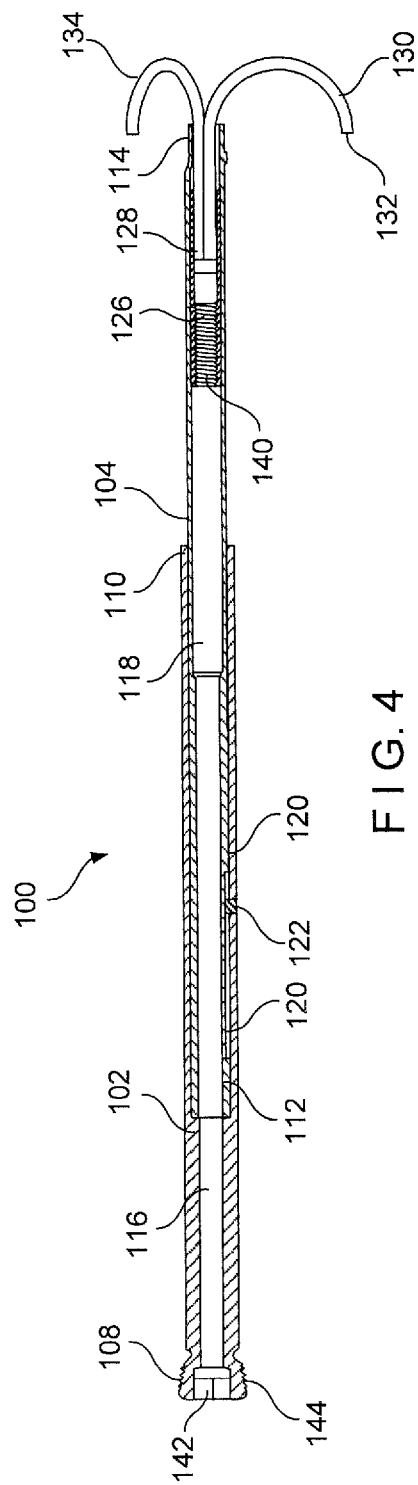
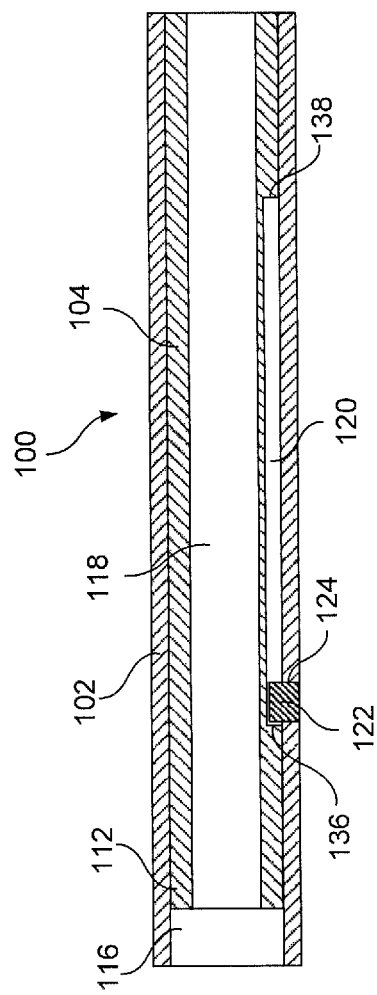

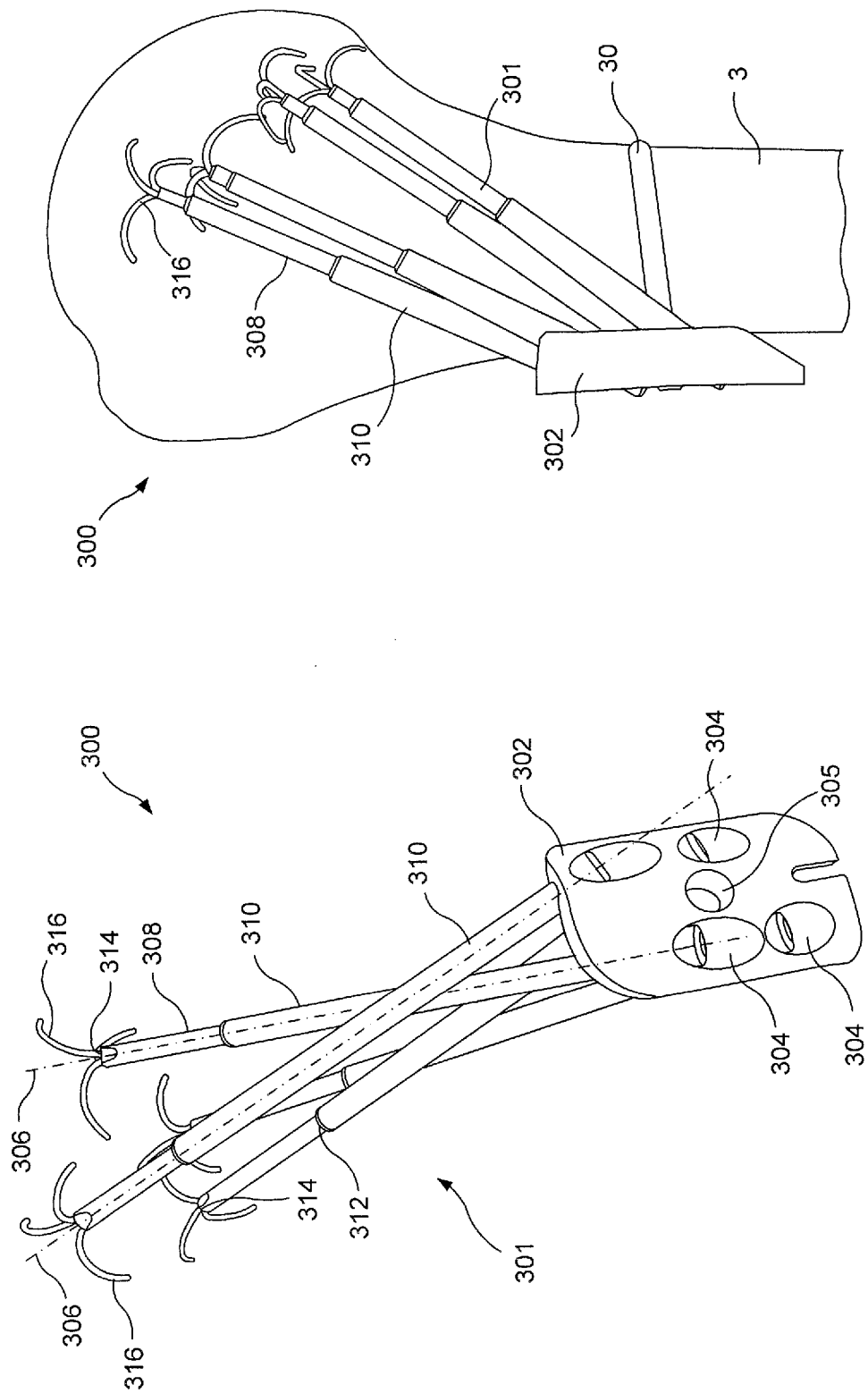

SHORTENING PALM SCREW

PRIORITY CLAIM

The present application claims priority to U.S. Provisional Application Ser. No. 61/537,874 entitled "Shortening Palm Screw" filed on Sep. 22, 2011 and U.S. Provisional Application Ser. No. 61/539,185 entitled "Shortening Palm Screw" filed on Sep. 26, 2011, the entire disclosures of which are incorporated herein by reference.

BACKGROUND

Proximal humerus fractures may be treated with angular stable implants inserted along a desired path into the head portion of the bone. In some cases, however, a distal end of the implant may penetrate the articular surface as the fracture heals, damaging the joint. Penetration may result in complications which require removal of the entire implant.

SUMMARY OF THE INVENTION

The present invention is directed to an implant for treating a bone, comprising an outer sleeve extending longitudinally from a proximal end to a distal end and including a lumen extending therethrough and an inner element sized and shaped to be slidably received within the lumen of the outer sleeve, the inner element extending longitudinally from a proximal end received within the lumen to a distal end including a bone-engaging element, the implant movable between an expanded configuration in which the inner element is in a distal-most position relative to the outer sleeve and a shortened configuration in which the inner element slides proximally relative to the outer element.

BRIEF DESCRIPTION OF THE DRAWINGS

FIG. 2 shows a longitudinal cross-sectional view of the implant of FIG. 1, in an expanded configuration;

FIG. 3 shows a longitudinal cross-sectional view of the implant of FIG. 1, in a deployed configuration;

FIG. 4 shows a longitudinal cross-sectional view of the implant of FIG. 1, in a shortened configuration;

FIG. 5 shows an enlarged cross-sectional view of a connection between inner and outer sleeves of the implant of FIG. 1;

FIG. 10 shows a perspective view system having a bone plate with a plurality of implants inserted therethrough;

FIG. 11 shows a side view of the system of FIG. 10 in an implanted configuration in the body;

DETAILED DESCRIPTION

Figure 1:
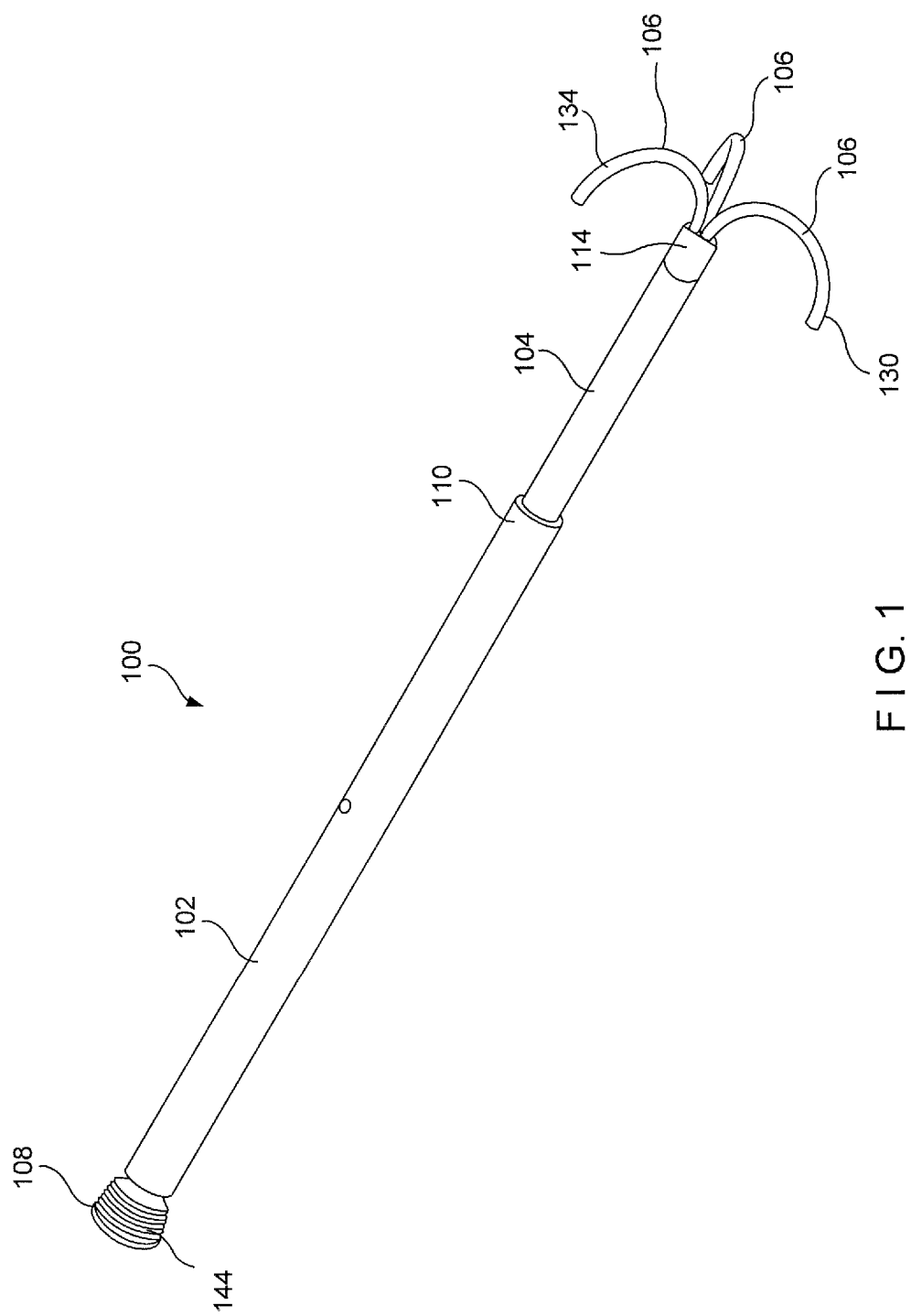
FIG. 1 shows a perspective view of an implant according to an exemplary embodiment of the present invention.

The present invention may be further understood with reference to the following description and the appended drawings, wherein like elements are referred to with the same reference numerals. The present invention relates to the treatment of fractures and, in particular relates to an angularly stable bone fixation device. Exemplary embodiments of the present invention describe an implant capable of shortening as the fracture heals to prevent penetration of an articular joint via a distal end of the implant. Although exemplary embodiment of the present invention specifically describe the fixation of a proximal humerus, it will be understood by those of skill in the art that the implant of the present invention may be used to fix a head portion of any long bone in the body such as, for example, the femur. It should also be noted that the terms "proximal" and "distal," as used herein, are intended to refer to a direction toward (proximal) and away from (distal) a user of the device.

As shown in FIGS. 1-5, an implant 100 for fixing a proximal humerus fracture comprises an outer sleeve 102 and an inner sleeve 104 slidably received within the outer sleeve 102. The outer and inner sleeves 102, 104 are coupled such that the outer and inner sleeves 102, 104 are longitudinally movable relative to one another within a predetermined range of motion while also being prevented from rotating relative to one another such that a torque may be applied to the outer sleeve 102, which is transferred to the inner sleeve 104. The implant 100 may be inserted along a desired path into a head portion of a target bone in an expanded configuration, as shown in FIG. 2, in which the inner sleeve 104 is in a distal-most position with respect to the outer sleeve 102. Once inserted, the inner sleeve 104 is permitted to slide proximally relative to the outer sleeve 102 to shorten the implant 100 as the bone fracture heals, as shown in FIG. 4. The implant 100 also includes a plurality of wires 106 housed within a distal end 114 of the inner sleeve 104, the plurality of wires 106 movable between an insertion configuration in which the plurality of wires 106 are housed entirely within the inner sleeve 104, as shown in FIG. 2, and a deployed configuration in which the plurality of wires 106 extend out of the distal end 114 and into the head portion of the target bone, as shown in FIG. 3.

The outer sleeve 102 extends along a longitudinal axis of the implant 100 from a proximal end 108 to a distal end 110 and includes a lumen 116 extending therethrough. The proximal end 108 may be configured to be coupled to a bone plate. For example, the proximal end 108 may include a threading 144 extending along an exterior thereof for engaging a threaded hole of a bone plate. The proximal end 108 may also include a recess 142 sized and shaped to engage a portion of a driver 150, as will be described in greater detail below. For example, the recess 142 may be hexagonal to engage a hexagonal portion of the driver 150. The inner sleeve 104 is sized and shaped to be received within the lumen 116 and extends along the longitudinal axis from a proximal end 112 to a distal end 114. The inner sleeve 104 also includes a lumen 118 extending therethrough. The proximal end 112 of the inner sleeve 104 is received within the lumen 116 of the outer sleeve 102 such that the outer and inner sleeves 102, 104 are longitudinally slidable relative to one another. The inner sleeve 104 includes a groove 120 extending along a portion of a length thereof, the groove 120 defining a permitted range of motion (i.e., a permitted length of shortening of the implant 100) between the outer and inner sleeves 102, 104.

In the exemplary embodiment shown in FIG. 5, the sleeves 102, 104 are substantially featureless. That is, the sleeves 102, 104 have a substantially smooth surface. However, as those skilled in the art would understand the surface of the sleeves 102, 104 could include one or more features according to the need or intended use of the implant 100. For example, one or both of the outer and inner sleeves 102, 104 could feature a screwthread. Where the inner sleeve 104 features the screwthread, the distal most part of the screwthread may, for example, end at a point that is proximal to the end of the outer sleeve 102 when the implant 100 is fully shortened.

As those skilled in the art would understand, the outer and inner sleeve 102, 104 may be connected to each other in a number of ways to shorten and transfer torque. For example, the lumen 116 and inner sleeve 104 may be complementarily shaped, such as hex-shaped, or faceted to transfer the torque and the inner sleeve 104 may comprise a stop member to limit the shortening. In an exemplary embodiment shown in FIG. 5, the outer and inner sleeves 102, 104 are connected to one another via a pin 122 received within a correspondingly sized and shaped opening 124 extending laterally through the outer sleeve 102. The pin 122 extends through the opening 124 of the outer sleeve 102 and into the groove 120. Thus, as the outer and inner sleeves 102, 104 move longitudinally relative to one another, the pin 122 slides along a length of the groove 120. The pin 122 and groove 120 are sized and shaped such that the outer and inner sleeves 102, 104 are permitted to move longitudinally relative to one another, but are prevented from rotating relative to one another. In the expanded configuration, the inner sleeve 104 is in a distal-most position relative to the outer sleeve 102. In other words, the pin 122 is positioned at a proximal-most end 136 of the groove 120. Once the implant 100 is inserted into the bone in the expanded configuration, the inner sleeve 104 is permitted to slide proximally relative to the outer sleeve 102 such that the pin 122 slides along the groove 120 toward a distal end 138 thereof. The groove 120 may be, for example, approximately 5 mm in length and the pin 122 may be, for example, 1 mm in length such that the implant 100 is permitted to shorten by a length of 4 mm.

The plurality of wires 106 are housed within the lumen 118 at the distal end 114 of the inner sleeve 104. The plurality of wires 106 are connected to the inner sleeve 104 via a connector bushing 126 which is longitudinally slidable within the lumen 118 to move the plurality of wires 106 between the insertion configuration and the deployed configuration. The connector bushing 126 includes a threading 140 along an interior surface thereof and may be coupled to a proximal end 128 of the plurality of wires 106, each of which may be circumferentially spaced about the connector bushing 126. In the insertion configuration, as shown in FIG. 2, the plurality of wires 106 are housed entirely within the lumen 118. In the deployed configuration, as shown in FIG. 3, the connector bushing 126 is slid distally relative to the inner sleeve 104 such that a distal portion 134 of the plurality of wires 106 extends distally past the distal end 114 of the inner sleeve 104 and into a surrounding bone to fix the implant 100 to the bone.

Each of the plurality of wires 106 extends from the proximal end 128 to a distal end 130, which may include a sharpened bone-penetrating distal tip 132. The plurality of wires 106 may be formed of a shape memory material such as, for example, Nitinol, such that the plurality of wires 106 are pre-shaped in the deployed configuration, shown in FIG. 3. In the deployed configuration, distal portions 134 extend distally past the distal end 114 of the inner sleeve 104 to penetrate the head portion of the bone in which the implant 100 has been inserted. In this embodiment, the wires 106 move toward a memorized shape in which they extend distally away from the distal end 114 for a distance and then bend back proximally to anchor the implant 100 to the bone. The plurality of wires 106 may be pre-shaped in the bent configuration in which the distal portion 134 is curved through approximately 90° and 180°. In the insertion configuration, as shown in FIG. 2, the plurality of wires 106 are held in a substantially straight configuration within the lumen 118 of the inner sleeve 104. However, as the plurality of wires 106 are moved to the deployed configuration, the distal portions 134 revert to the bent configuration, as the distal end 130 pierces through the bone.

Figure 6:
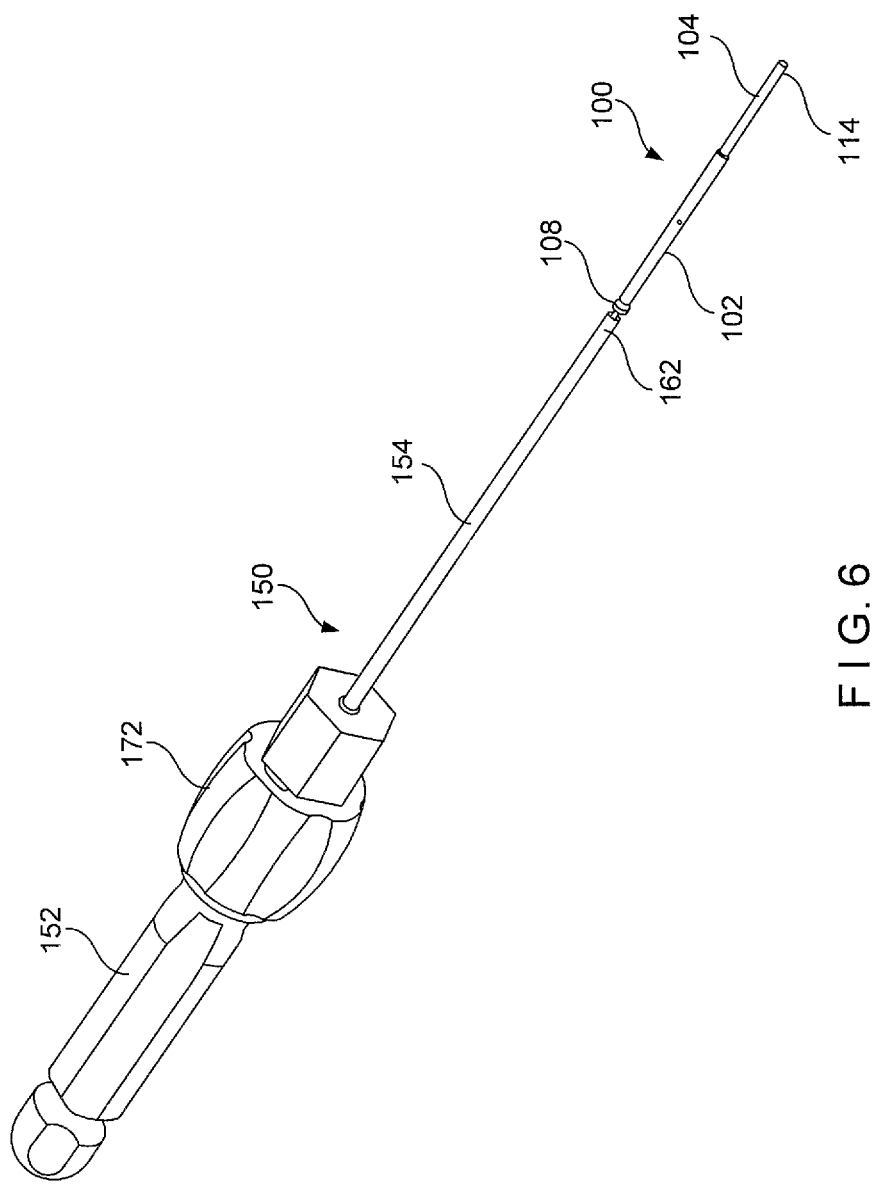
FIG. 6 shows a perspective view of a driver according to an exemplary embodiment of the present invention, in a first configuration.
Figure 7:
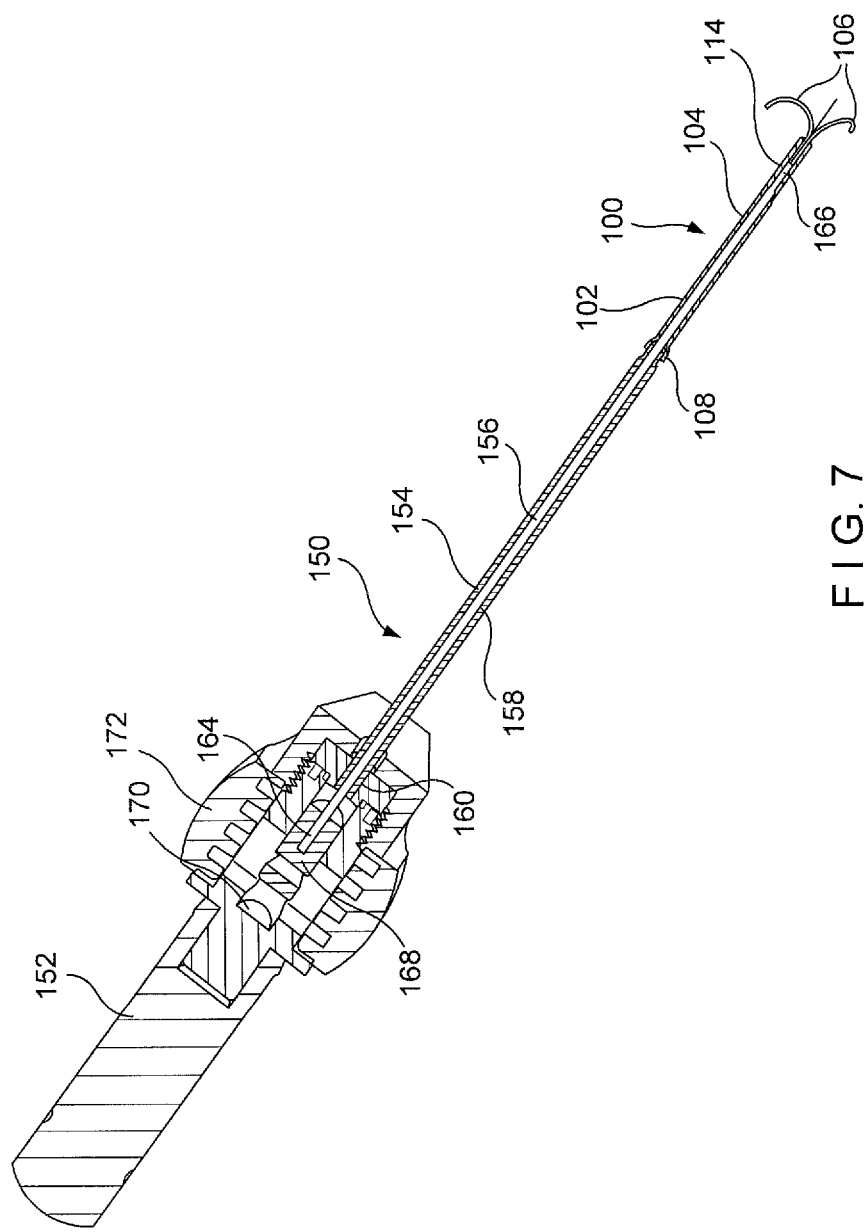
FIG. 7 shows a longitudinal cross-sectional view of the driver of FIG. 6, in a second configuration.
Figure 8:
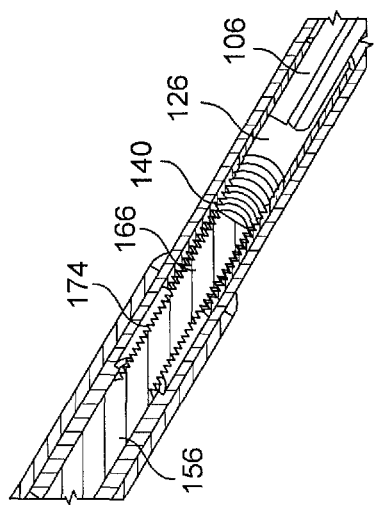
FIG. 8 shows an enlarged cross-sectional view of a distal portion of the driver of FIG. 6.

The implant 100 may be inserted into the target bone using the driver 150, as shown in FIGS. 6-7. The driver 150 comprises a handle 152 coupled to a shaft 154. The shaft 154 extends longitudinally from a proximal end 160 connected to the handle 152 to a distal end 162 sized and shaped to engage the recess 142 of the outer sleeve 102 of the implant 100. The distal end 162 may, for example, be hexagonally shaped to engage a hexagonal recess 142. Thus, rotating the handle 152 about a longitudinal axis thereof, correspondingly rotates the shaft 154 and the implant 100 coupled thereto such that the implant 100 may be driven into the target bone. The shaft 154 also includes a lumen 158 extending longitudinally through the shaft 154 to receive a pusher element 156 therein.

As those skilled in the art would understand, any mechanism or device can be used to deploy the plurality of wires 106. For example, a rod may be pushed or hammered through the shaft to engage with the proximal portion of the plurality of wires 106. In the exemplary embodiment shown in FIGS. 6 and 7, the driver 150 includes a pusher element 156. The pusher element 156 extends through the shaft 154 longitudinally from a proximal end 164 to a distal end 166. The proximal end 164 is movably coupled to the handle 152 via a block 168 which is housed within a channel 170 of the handle 152 and movable relative thereto along a length of the channel 170. The block 168 is moved longitudinally relative to the channel 170 via a knob 172 which threadedly engages the handle 152. Rotating the knob 172 relative to the handle 152 moves the pusher element 156 longitudinally relative to the handle 152 and the shaft 154. Thus, the pusher element 156 is movable between a first position, in which the pusher element 156 is at a proximal-most position relative to the handle 152 and shaft 154, and a second position, in which the pusher element 156 is at a distal-most position relative to the handle 152 and shaft 154. The distal end 166 of the pusher element 156 includes a threading 174 therealong for engaging the threading 140 of the connector bushing 126.

A length of the pusher element 156 is selected such that when the driver 150 is in the first configuration (i.e., the pusher element 156 is in a proximal-most position relative to the handle 152 and the shaft 154) and is coupled to the implant 100, the threading 174 at the distal end 166 of the pusher element 156 engages the threading 140 of the connector bushing 126 to maintain the implant 100 in the expanded configuration. In addition, the position of the connector bushing 126 relative to the inner sleeve 104 maintains the plurality of wires 106 in the insertion configuration during insertion of the implant 100 into the bone. In this configuration, the driver 150 may be used to apply a rotative force to the implant 100 to insert the implant 100 into the target bone. The implant 100 may also be rotated such that the proximal end 108 of the outer sleeve 102 may engage a threaded hole of a bone plate. Once the implant 100 has been inserted into the bone, the driver 150 may be moved to the second configuration by rotating the knob 172 relative to the handle 152 to move the pusher element 156 distally with respect to the shaft 154 such that the pusher element 156 pushes the connector bushing 126 and the plurality of wires 106 distally with respect to the inner sleeve 104 and into the surrounding target bone. Once the implant 100 has been implanted, as desired, the driver 150 may be removed by simply drawing the handle 152 and shaft 154 proximally to disengage the distal end 162 of the shaft 154 from the recess 142. The pusher element 156 may then be rotated to disengage the threading 174 at the distal end 166 thereof from the threading 140 of the connector bushing 126. Upon removal of the driver 150, the implantation of the implant 100 is complete.

According to an exemplary embodiment of a surgical technique, the implant 100 may be inserted along a desired path into the head portion of the target bone, in the expanded configuration, using the driver 150. The driver 150 is coupled to the implant 100 in the first configuration such that coupling the driver 150 to the implant 100 maintains the implant 100 in the expanded configuration, as shown in FIG. 2. In particular, the distal end 162 of the shaft 154 of the driver 150 engages the recess 142 of the implant 100 such that the distal end 166 of the pusher element 156 extends through the lumens 116, 118 of the outer and inner sleeves 102, 104, respectively, to engage the connector bushing 126. The implant 100 may then be inserted through a hole of a bone plate and rotated relative thereto via the driver 150 such that the threading 144 at the proximal end 108 of the outer sleeve 102 engages a corresponding threading of the bone plate hole.

Once the implant 100 has been inserted into the bone in the expanded configuration, the driver 150 is moved to the second configuration by rotating the knob 172 relative to the handle 152 to move the pusher element 156 distally with respect to the shaft 154. The distal motion of the pusher element 156 pushes the connector bushing 126, and thereby the plurality of wires 106, distally with respect to the inner sleeve 104 into the deployed configuration, shown in FIG. 3. Once the implant 100 has been inserted into the bone and the plurality of wires 106 have been deployed, the driver 150 may be removed, as described above. As the fracture in the target bone heals, the inner sleeve 104 may slide proximally with respect to the outer sleeve 102, as described above, to permit the implant 100 to shorten, as shown in FIG. 4. It will be understood by those of skill in the art that shortening of the implant will reduce the risk of penetration of the articular surface of the target bone.

Figure 9:
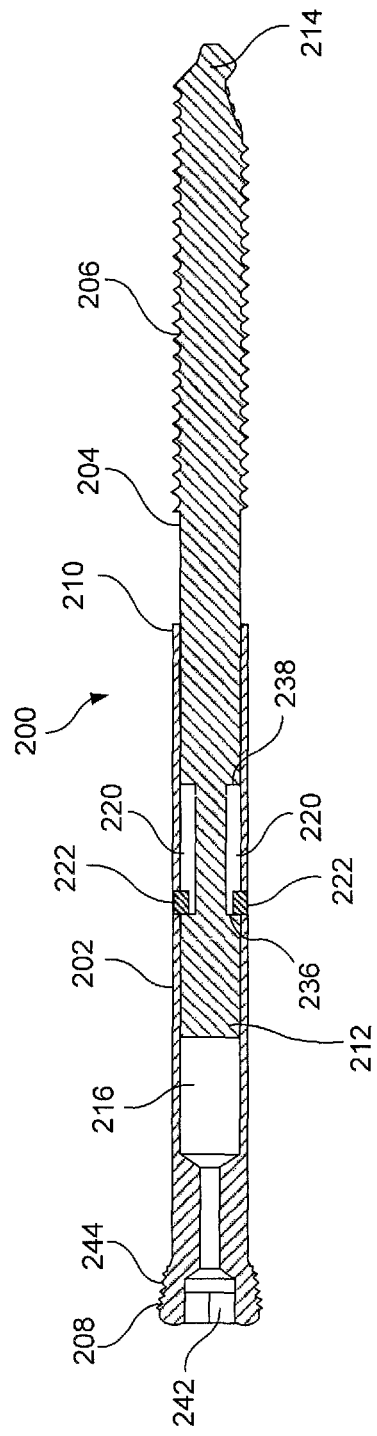
FIG. 9 shows a longitudinal cross-sectional view of an implant according to another exemplary embodiment of the present invention.

As shown in FIG. 9, an implant 200 according to an another exemplary embodiment of the present invention may be substantially similar to the implant 100, comprising an outer sleeve 202 and an inner element 204, which are longitudinally movable with respect to one another between an expanded configuration, in which the inner element 204 is in a distal-most position with respect to the outer sleeve 202, and a shortened configuration, in which the inner element 204 is permitted to slide proximally relative to the outer sleeve 202. Similarly to the implant 100, the outer sleeve 202 and the inner element 204 may be connected to one another via a pin 222 and a groove 220 extending along the inner element 204. The implant 200, however, may include a pair of pins 222 and grooves 220 positioned on diametrically opposing sides of the implant 200.

The outer sleeve 202 may be substantially similar to the outer sleeve 102 extending longitudinally from a proximal end 208 to a distal end 210 and including a lumen 216 extending therethrough. The proximal end 208 may include a threading 244 along an exterior thereof for engaging a corresponding threading of a bone plate hole and may also include a recess 242 for engaging a portion of a driver. Similarly to the inner sleeve 104, the inner element 204 is sized and shaped to be slidably received within the outer sleeve 202 and extends from a proximal end 212 to a distal end 214. The inner element 204, however, does not house any wires, but rather, includes a threading 206 extending along a distal portion thereof for engaging a bone. Thus, the implant 200 may be inserted along a desired path into a target bone, in the expanded configuration in which the inner element 204 is in a distal-most position relative to the outer sleeve 202 and the pin 222 is at a proximal end 236 of the groove 220. It will be understood by those of skill in the art that the implant 200 may be rotatively driven into the bone, substantially similarly to the implant 100, using a driver which engages the recess 242 such that the threading 206 engages the target bone. Once the implant 200 has been implanted into the bone, as desired, the implant is permitted to shorten as the bone fracture heals. In particular, the inner element 204 is permitted to slide proximally with respect to the outer sleeve 202 such that the pin 222 slides toward a distal end 238 end of the groove 220. It will be understood by those of skill in the art that the implant 200 may be inserted into the target bone in a manner substantially similar to the implant 100, as described above.

FIGS. 10-11 depicts a system 300 according to another embodiment of the invention. The implant 300 includes a bone plate 302 configured to receive a plurality of implants 301 therethrough. The implants 301 may be substantially similar to any of the implants 100, 200 described earlier. The system 300 provides a minimally invasive, semi-rigid angularly stable fixation of two-part proximal humeral fractures. It is noted that the implant 300 may also be used for the fixation of any multi-part proximal humeral fractures without deviating from the scope of the invention. The exemplary system and method disclosed hereinafter allow for sintering of head fragments to permit and maintain fracture compression during the healing process. The implant 300 comprises a stainless steel humerus bone plate 302 including, for example, four angular stable locking compression plate holes 304 extending therethrough. Each of the holes 304 extends through the plate 302 at a predetermined angle defining a respective hole axis 306 aligned with a longitudinal axis of s telescoping implant 301 inserted therethrough, as will be described in greater detail later on. It is noted that any number, position and orientation of the holes 304 may be used without deviating from the scope of the invention. At least a distal portion of some or all of the holes 304 may include threading (not shown) configured to engage threads provided on an outer surface of a proximal end (not shown) of the fixation pins 308 to provide a locking engagement between the plate and a corresponding implant 301 as would be understood by those skilled in the art.

Each of the implants 301 may be formed substantially similarly to any of those described in earlier embodiments and including, for example, inner and outer sleeves 308, 310 substantially similar to the inner and outer sleeves 104, 102. Specifically, the inner and outer sleeves 308, 310 are longitudinally movable with respect to one another between an expanded configuration, in which the inner element 308 is in a distal-most position with respect to the outer sleeve 310, and a shortened configuration, in which the inner element 308 has slid proximally relative to the outer sleeve 310. Similarly to the implants 100, 200 the outer sleeve 310 and the inner sleeve 308 may be connected to one another via a pin and groove arrangement (not shown) comprising any number of pins and grooves.

The outer sleeve 310 may be substantially similar to either of the outer sleeves 102, 202 extending longitudinally from a proximal end (not shown) to a distal end 312 and including a lumen extending therethrough. The proximal end (not shown) may include a threading (not shown) along a portion of an exterior thereof for engaging a corresponding threading of the plate hole 304 and may also include a recess (not shown) for engaging a portion of a driver. The inner sleeve 308 is sized and shaped to be slidably received within the outer sleeve 310 and extends from a proximal end (not shown) to a distal end 314. The implant 301 also includes a plurality of wires 316 housed within a distal portion of the inner sleeve 308. The wires 316 are movable between an insertion configuration in which the distal portions of the wires 316 are housed entirely within the inner sleeve 308, and a deployed configuration in which distal portions of the wires 316 extend distally from the distal end 314 and into the head portion of a target bone 3, as shown in FIGS. 10-11. As described in greater detail in regard to the earlier embodiments, the implant 301 is configured to allow for up to 5 mm axial shortening thereof under load (i.e., after implantation). The wires 316 include, for example, three pre-bent 0.7 mm Nitinol springs deployable in situ after placement and locking of the implants 301 in the bone. In an extended state, the three curved wires 316 improve fixation of the implant 301 in cancellous bone and prevent perforation thereof into the glenohumeral joint.

The bone plate 302 comprises a locking hole 305 extending therethrough (e.g., substantially perpendicular to a longitudinal axis of a target bone). In an operative configuration, a bone screw 30 is inserted through the locking hole 305 to lock a position of the bone plate 302 over the bone, as those skilled in the art will understand. It is further noted that the locking hole 305 may extend through the bone plate 302 at any angle selected to conform to the requirements of a target bone and/or procedure.

Figure 12:
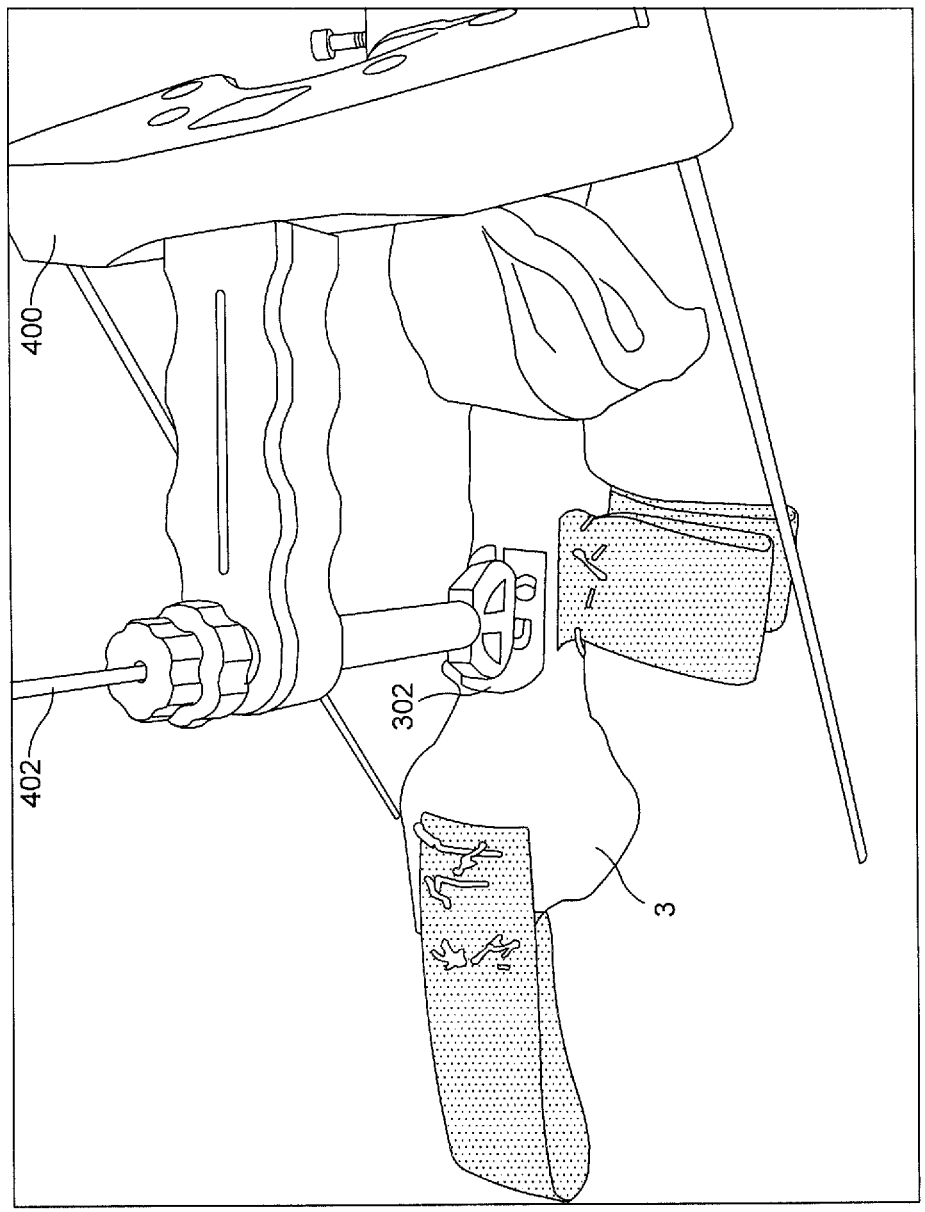
FIG. 12 shows the bone plate of FIG. 10 in an insertion configuration with an aiming device.

In accordance with an exemplary method according to the invention, the bone plate 302 may be attached to an aiming device 400, as shown in FIG. 12. As those skilled in the art will understand, the aiming device 400 may use any number of Kirschner wires 402 or other suitable devices to maintain a desired position of the bone plate 302 over the bone 3. It is noted that the bone 3 depicted in FIG. 12 is shown ex-situ. In an in-situ bone fixation procedure, the Kirschner wires 402 may be inserted through any portion of the aiming device into a target portion of bone, as those skilled in the art will understand. In the exemplary procedure, the bone plate 302 is provisionally fixed to a humeral shaft of the bone 3 via a Kirschner wire 402 inserted through the aiming device 400 and the locking hole 305. Four additional Kirschner wires 402 are then driven through drill guides (not shown) inserted through aiming device holes, through the holes 304 and into the humeral head. The correct positioning of the k-wires may be verified, for example, under fluoroscopic observation. A cannulated drill is used to open the path for the implants 301 pins along the axis of the k-wires. The implants 301 are inserted in the fully extended position through the drill guides of the aiming device 400. The wires 316 are then deployed and fixed, as described in greater detail in earlier embodiments. Finally, the aiming device 400 is removed and the plate 302 is attached to the shaft with an angularly stable LCP screw 30 inserted through the locking hole 305.

The system and method disclosed herein have been heavily tested to ensure that the system 300 allows for angularly stable dynamic fixation of two part proximal humeral fractures by enabling closure of a fracture gap and maintenance of fracture compression during loading. Specifically, biomechanical testing was performed using a shoulder test bench developed to simulate cyclic loading in abduction and adduction induced by active muscle forces. The muscles were attached to the original insertions of the supraspinatus, the deltoid muscle, the teres major and the major pectoralis. Abduction was simulated in the plane of the scapula without humeral internal rotation. In order to restrict motion to the desired plane an arc rail was used for guidance. The shoulder test bench includes a polyethylene glenoid used for guidance of the humeral head during motion. The glenoid was connected to a 6-component load cell recording forces during cyclic loading. Load cells in line with the pneumatic muscles were used to monitor applied muscle forces during testing. The specimen was distally embedded in PMMA and attached to a linear bearing allowing translation in the axis of the humeral shaft. This translation compensates for the varying radius of the humeral head and the fracture gap motion. The degree of abduction was recorded by an inclinometer. The weight of the arm is assumed as 3.75 kg with a lever arm of 300 mm representing a patient weight of approximately 75 kg as previous research reported the weight of the arm to be 5% of the total body weight.

Data was collected and recorded on a personal computer using a custom written Lab View application (National Instruments, Austin, Tex.) for data collection and control of the pneumatic muscles. To evaluate varus tilting of the fracture gap, as well as sintering of the humeral head during testing a three-dimensional motion analysis system (Winbiomechanics, Zebris, Isny, Germany) was mounted to the plate of the Humerusblock NG fixed to the humeral shaft and the humeral head. The specimen included six fresh frozen human upper extremities for which quantitative computed tomographies (qCT, General Electrics, Lightspeed VCT 64) were performed to exclude pathologies affecting the bone structure integrity. Based on the CT datasets measurement of the cancellous bone mineral density (BMD) was performed according to the method described by Krappinger et al. To evaluate a possible impact of bone mineral density on the fixation stability of the Humerusblock NG specimens with different BMDs ranging from severe osteoporotic to normal were chosen. The specimens were stored at −20° C. until further processing. Prior to preparation, specimens were thawed overnight at 6° C. All soft tissue was carefully removed except for the ligamentous insertions of the supraspinatus muscle, the deltoid muscle, the teres major and the pectoralis major. The humeri were cut 6.5 cm distally to the distal insertion of the deltoid muscle and embedded in PMMA. Webbing straps were sutured to the ligamentous insertions of the supraspinatus, teres major, and pectoralis major for attachment to the pneumatic muscles. The insertion of the deltoid muscle was connected to two polyamide cables using a custom made clamp. After creation of the fracture models the Humerusblock NG was implanted by a board certified trauma surgeon. During preparation and cyclic testing each specimen was kept moist using saline solution.

Abduction and adduction were simulated between 15° and 45°. Two different fracture models were created. Initially, a wedge osteotomy with a lateral fracture gap of 0.5 cm was performed 1 cm below the medial border of the anatomical neck to mimic a stable two-part fracture. After implantation of the Humerusblock NG the construct was loaded for 500 cycles. Thereafter, the medial hinge was resected to create a fracture gap of 0.5 cm to simulate an unstable fracture. The construct was loaded for another 500 cycles. All data were recorded for the first 40 cycles and thereafter every $20^{th}$ and $21^{st}$ cycle. To evaluate fracture gap compression in the course of cyclic loading the per cycle and maximum displacement of the humeral head relative to the shaft in the longitudinal axis of the humerus was analyzed. For assessment of the varus tilt per cycle and maximum rotation of the head towards the shaft in the scapular plane was measured.

Standardized plain ap and lateral x-rays of the constructs were performed before the testing and after every 500 cycles (with and without medial hinge) to measure implant migration. The upper right pin was defined as pin 1, the upper left pin as pin 2, the lower right pin as pin 3, and the lower left pin as pin 4. The tip-apex distance (TAD) between the tips of the pins and the cortex of the humeral head in the axis of the pins in the ap and lateral view was measured. Furthermore, changes in the length of each telescoping pin in the ap view were measured. Statistical analysis was performed using SPSS 18.0 (Chicago, Ill.). Data comparison was performed using a one way repeated measures ANOVA with Bonferroni correction for multiple comparisons. None of the specimens failed during the testing and no cases of implant breakage or fixation pin perforation were observed. The mean BMD was 92.25 mg/cm$^3$ (range: 69.4-136 mg/cm$^3$). The mean maximum resulting force on the glenoid was 609 N (SD: 52 N) during cyclic loading. The average maximum muscle forces during cyclic loading were: 202 N (SD: 32 N) for the supraspinatus, 498 N (SD: 51) for the deltoid muscle, 43 N (SD: 7 N) for the major pectoralis, and 49 N (SD: 8 N) for the teres major.

Figure 13:
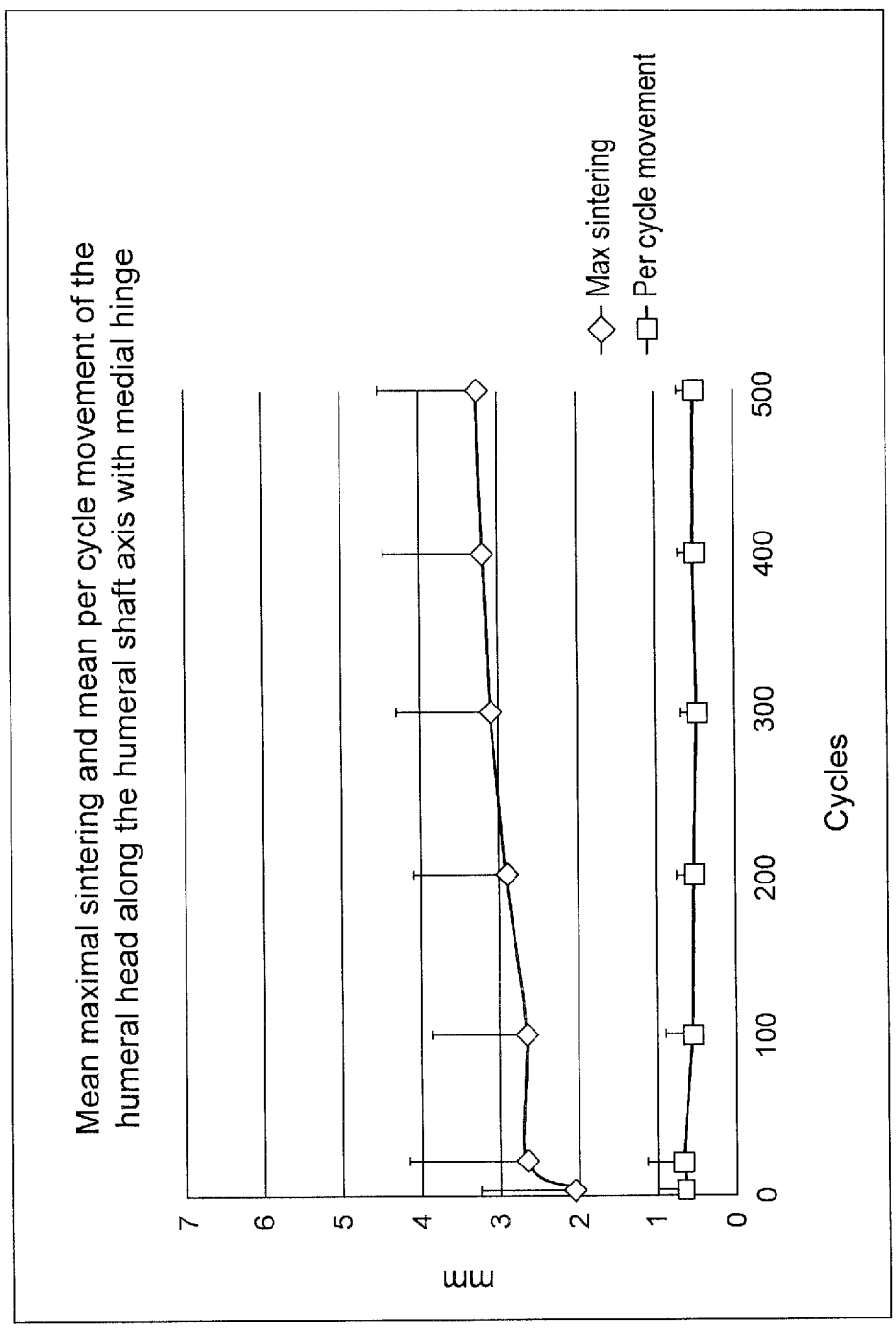
FIG. 13 depicts a graph showing mean maximal sintering and mean per cycle movement of the humeral head along the humeral shaft axis with medial hinge.
Figure 14:
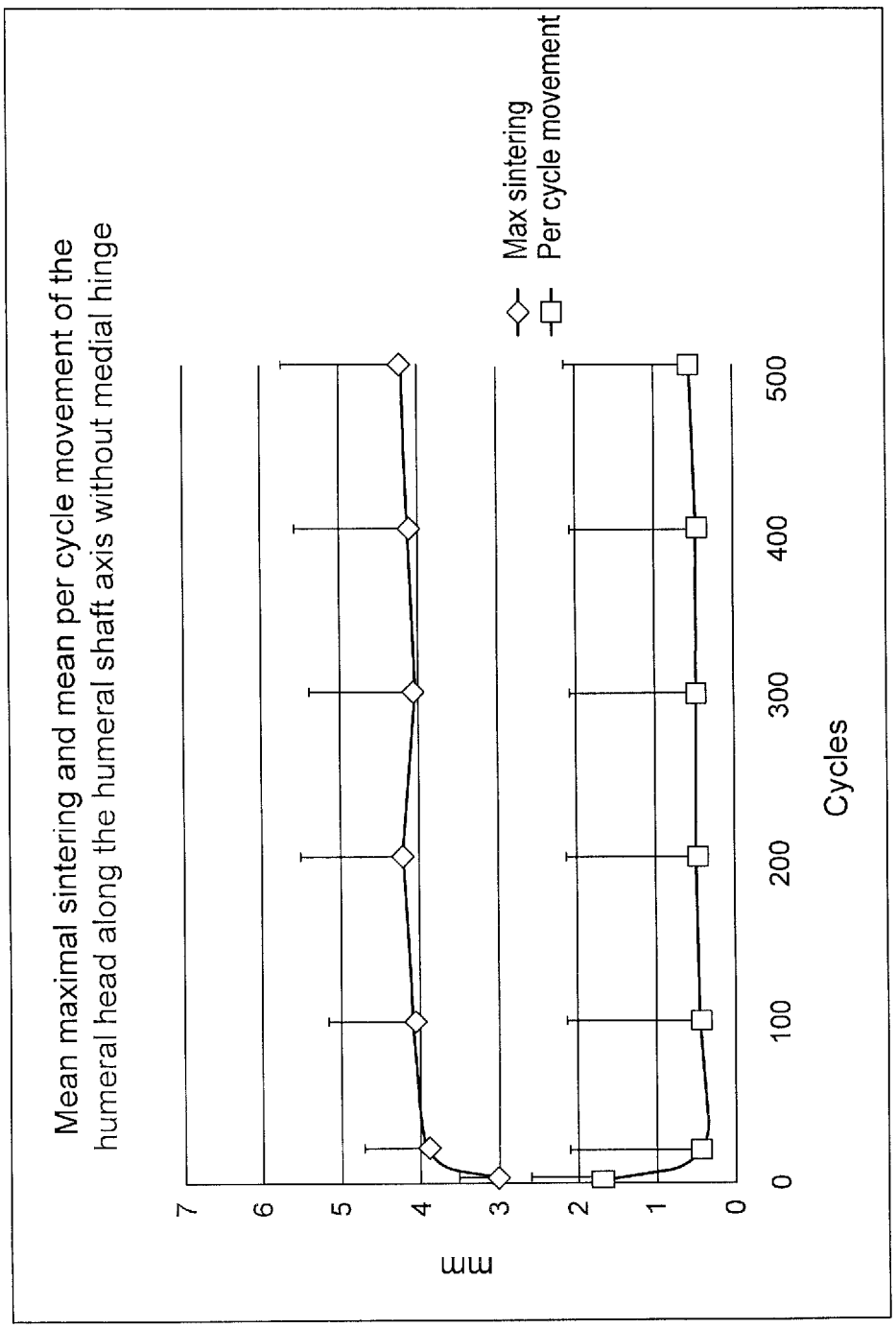
FIG. 14 depicts a graph showing mean maximal sintering and mean per cycle movement of the humeral head along the humeral shaft axis without medial hinge.
Figure 15:
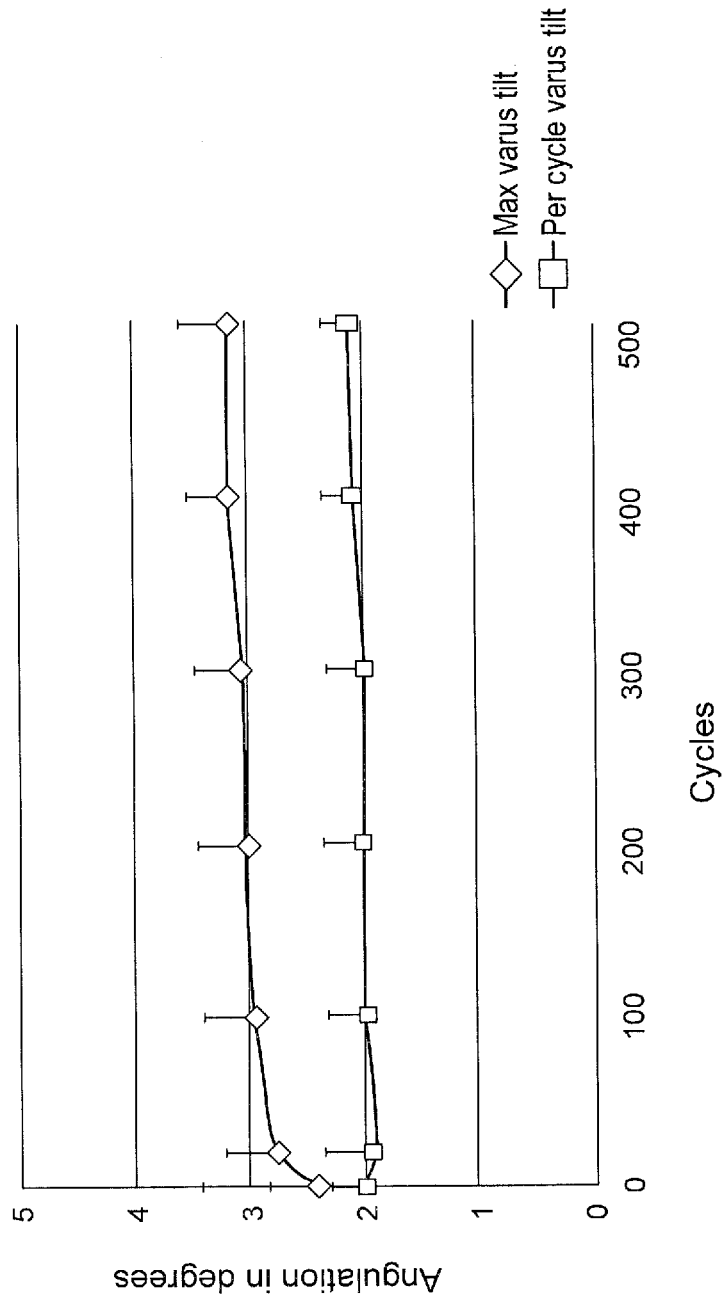
FIG. 15 depicts a graph showing man maximum varus tilt and per cycle varus tilt of the humeral head with medial hinge.
Figure 16:
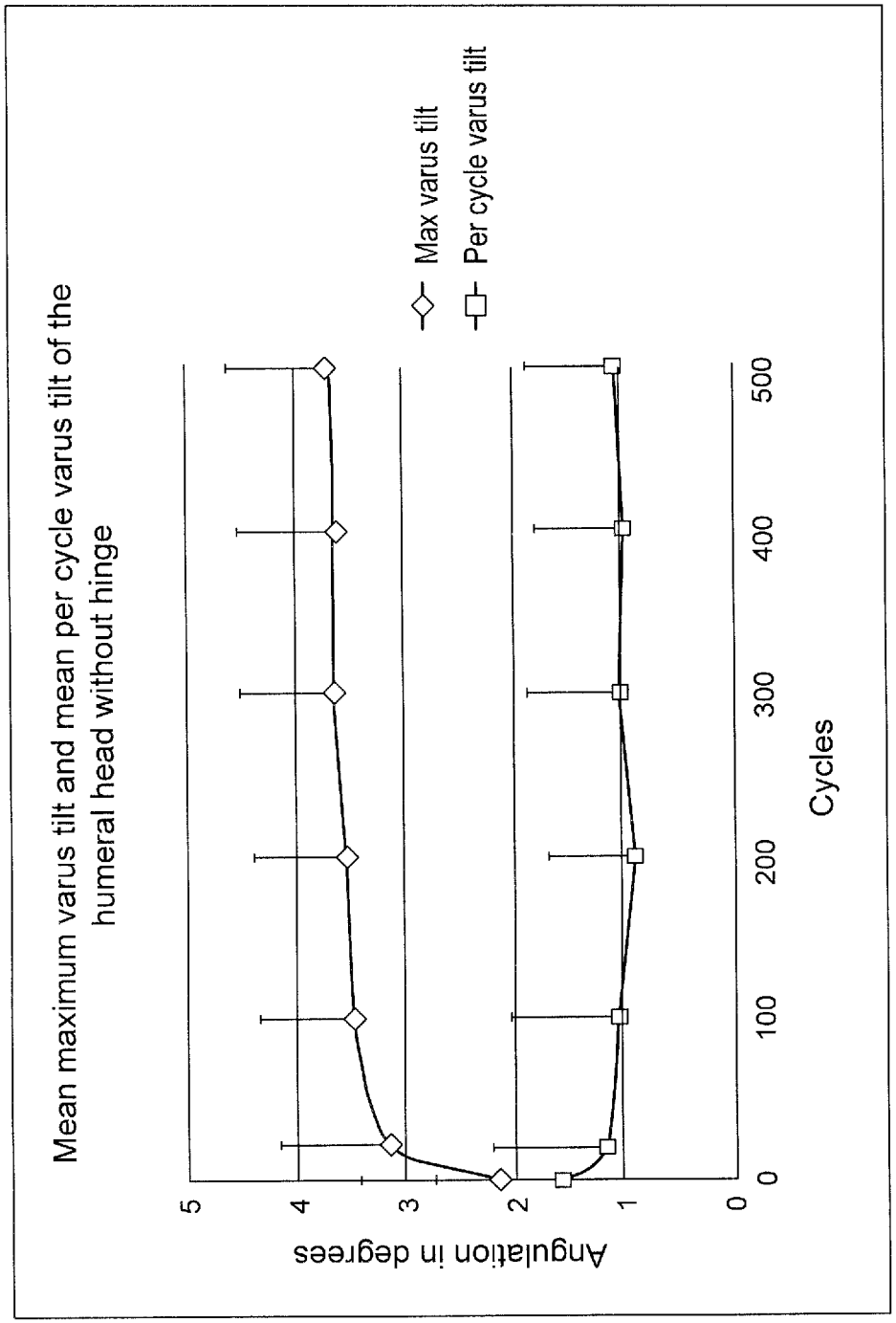
FIG. 16 depicts a graph showing man maximum varus tilt and per cycle varus tilt of the humeral head without hinge.

With medial hinge the fracture showed a mean maximum sintering of the head fragment along the humeral shaft axis of 3.22 mm (SD: 1.25 mm), as shown in FIG. 13 after 500 cycles. The fracture without medial hinge showed initial closure of the fracture gap and only slow sintering thereafter. After 500 cycles the humeral head showed a mean maximum sintering of 4.27 mm (SD: 1.53 mm), as shown in FIG. 14. Mean per cycle motion of the fracture gap with medial hinge along the humeral shaft axis was 0.51 mm (SD 0.22 mm) at the end of the cyclic loading, as shown in FIG. 13. The fracture model without medial hinge showed a comparable mean per cycle movement of 0.60 mm (SD: 1.53 mm) after 500 cycles, as shown in FIG. 14. Mean maximum varus tilt of the humeral head with medial hinge was 3.17° (SD: 0.44°), as shown in FIG. 15. The fracture model without medial hinge showed a mean maximum varus tilt of 3.68° (SD: 0.93°) after 500 cycles, as shown in FIG. 16. Mean per cycle varus tilt after 500 cycles was 2.11° (SD: 0.23°) (FIG. 15) with medial hinge and 1.07° (SD: 0.82°) (FIG. 16) without medial hinge.

Figure 17:
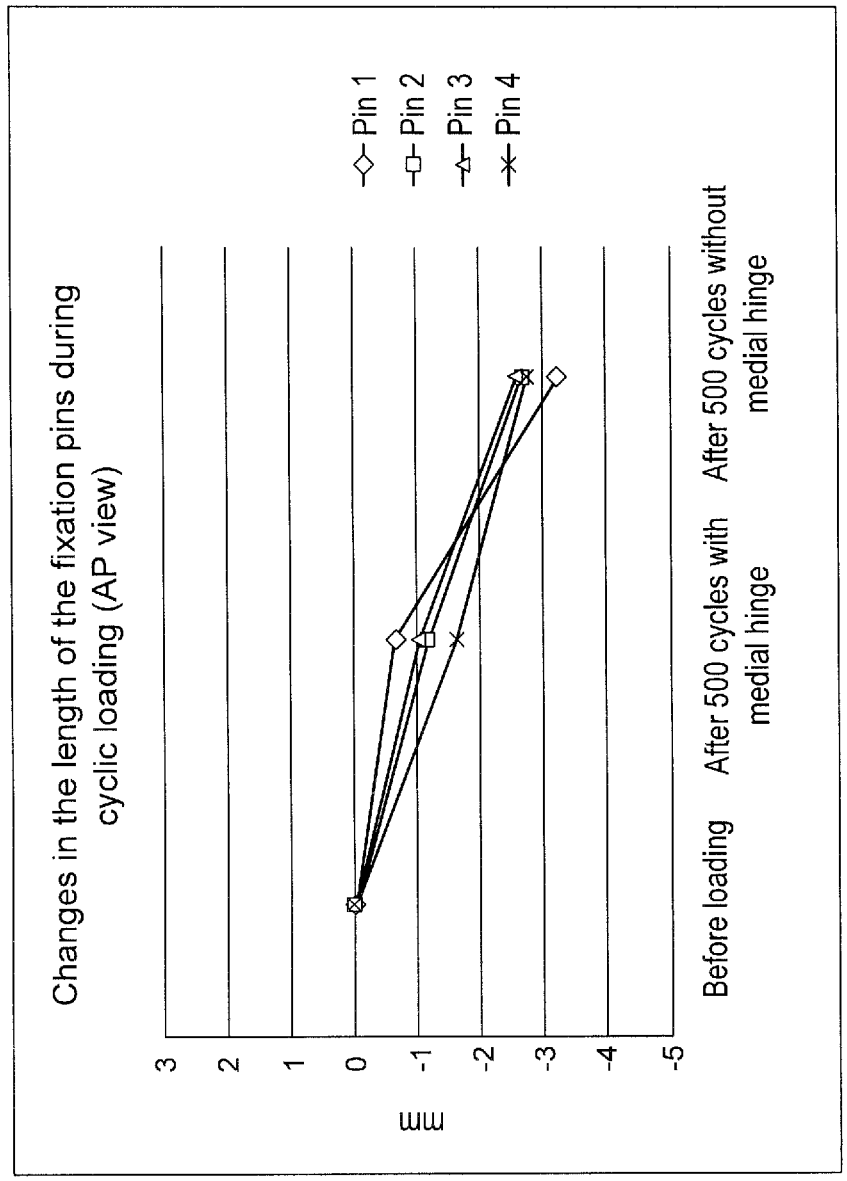
FIG. 17 depicts a graph showing changes in the length of the telescoping fixation pins during cyclic loading.

After 500 cycles of loading with medial hinge the mean change of the radiological TAD of the four pins was 0.20 mm (SD: 0.49 mm) in the AP and −0.04 mm (SD: 0.15 mm) in the lateral view, as shown in Table 1 below. After 500 cycles of loading without medial hinge the mean change of TAD was −0.41 mm (SD: 0.52) in the AP and −0.26 mm (SD 0.32) in the lateral view. Overall, statistical analysis showed no significant change in the TAD of any pin tip after cyclic loading. In contrast, the mean change of the length of the fixation pins after 500 cycles of loading with medial hinge was −1.1 mm (SD: 0.39 mm) in the AP view. This difference did not reach statistical significance. After 500 cycles of loading without medial hinge a significant shortening of the mean length of the fixation pins of −2.8 mm (SD: 0.29 mm) could be measured. This decrease of length was statistically significant for all pins (p<0.38) (FIG. 17).

TABLE 1

Change of the mean tip apex distance (mm) of the fixation pins after cyclic load Changes in the mean TAD in mm after cyclic loading

| Pin | 500 cycles with medial hinge | | 500 cycles without medial hinge | |
| --- | --- | --- | --- | --- |
|  | AP | lateral | AP | lateral |
| 1 | 0.96 (SD: 1.43) | −0.21 (SD: 0.45) | −0.08 (SD: 2.92) | −0.40 (SD: 0.65) |
| 2 | 0.06 (SD: 1.35) | 0.01 (SD: 0.40) | −0.95 (SD: 1.35) | −0.37 (SD: 0.60) |
| 3 | −0.41 (SD: 1.12) | −0.12 (SD: 0.97) | −0.76 (SD: 1.78) | −0.47 (1.25) |
| 4 | 0.18 (SD: 2.39) | 0.14 (SD: 0.93) | 0.13 (SD: 1.99) | 0.21 (SD: 0.78) |

It will be apparent to those skilled in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. An implant for treating a bone, comprising:
an outer sleeve extending longitudinally from a proximal end to a distal end and including a lumen extending therethrough; and
an inner element sized and shaped to be slidably received within the lumen of the outer sleeve, the inner element extending longitudinally from a proximal end received within the lumen to a distal end, the inner element housing a bone-engaging element therein, the implant is movable from an expanded configuration in which the inner element is in a distal-most position relative to the outer sleeve and the bone-engaging element extends out of the distal end of the inner element, to a shortened configuration in which the inner element slides proximally relative to the outer element and the bone-engaging element is housed within the inner element.

2. The implant of claim 1, wherein a coupling arrangement between the inner element and the outer sleeve is configured to permit a range of shortening of the implant and to transfer a rotational force applied to the outer sleeve to the inner element.

3. The implant of claim 2, wherein the coupling arrangement comprises a pin extending into a groove, the groove dimensioned to define the permitted range of shortening of the implant.

4. The implant of claim 3, wherein the pin extends laterally from the outer sleeve into the groove.

5. The implant of claim 1, wherein the proximal end of the outer sleeve includes a threading configured to engage a corresponding threading of a bone plate hole.

6. The implant of claim 1, wherein the bone-engaging element includes a plurality of wires movable between an insertion configuration in which distal ends of the wires are housed within a lumen of the inner element and a deployed configuration in which the distal ends of the wires extend distally out of an opening at the distal end of the inner element to penetrate a portion of bone adjacent to the distal end of the inner element, the wires being biased to assume an anchoring shape when extended out of the elongated body.

7. The implant of claim 6, wherein the plurality of wires are connected to the inner element via a connector bushing longitudinally slidable within the lumen of the inner element.

8. The implant of claim 6, wherein, when in the anchoring shape, the wires extend distally from the inner element a first distance and then curve radially away from a longitudinal axis of the implant.

9. The implant of claim 8, wherein, when in the anchoring shape, the wires curve through an angle of between approximately 90° and 180°.

* * * * *